United States Patent

Naepfli et al.

[11] Patent Number: 5,856,483
[45] Date of Patent: Jan. 5, 1999

[54] PROCESS FOR PREPARING 4,6-BIS(DIFLUOROMETHOXY)PYRIMIDINE DERIVATIVES

[75] Inventors: Andreas Naepfli, Glis; Jean-Paul Roduit, Grône; Alain Wellig, Ried-Mörel, all of Switzerland

[73] Assignee: Lonza AG, Gampel/Valais, Switzerland

[21] Appl. No.: 893,228

[22] Filed: Jul. 15, 1997

[30] Foreign Application Priority Data

Jul. 24, 1996 [CH] Switzerland ................ 1846/96

[51] Int. Cl.⁶ .................................................. F07D 239/60
[52] U.S. Cl. ............................................................ 544/303
[58] Field of Search ............................................. 544/303

[56] References Cited

U.S. PATENT DOCUMENTS 4,692,524  9/1987  Hässig ........................................ 544/303
4,900,827  2/1990  Seifert et al. ............................. 544/303

FOREIGN PATENT DOCUMENTS 0 468 069  1/1992  European Pat. Off. .
0 529 631  3/1993  European Pat. Off. .

*Primary Examiner*—John M. Ford
*Attorney, Agent, or Firm*—Fisher, Christen & Sabol

[57] ABSTRACT

A process for preparing 4,6-bis(difluoromethoxy)pyrimidine derivatives of the general formula:

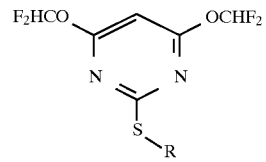

wherein R is a $C_{1-4}$-alkyl or optionally substituted phenyl or benzyl, proceeding from the corresponding 4,6-dihydroxypyrimidine dialkali-metal salt. In the process, the educt is reacted under pressure with chlorodifluoromethane in a solvent selected from the group consisting of the ketones, in the presence of a base and a phase-transfer catalyst and in the presence of 40 to 100 mol per mol of water of the 4,6-dihydroxypyrimidine dialkali-metal salt to form the final product.

15 Claims, No Drawings

PROCESS FOR PREPARING 4,6-BIS(DIFLUOROMETHOXY)PYRIMIDINE DERIVATIVES

BACKGROUND OF THE INVENTION

1. Field of the Invention

The invention relates to a novel process for preparing 4,6-bis(difluoromethoxy)pyrimidine derivatives proceeding from 4,6-dihydroxypyrimidine dialkali-metal salts.

2. Background Art 4,6-bis(difluoromethoxy)pyrimidine derivatives are important intermediates for producing herbicides, for example, for producing sulfonylureas (U.S. Pat. No. 4,900,827).

Hitherto, a plurality of processes have been disclosed for preparing 4,6-bis(difluoromethoxy)pyrimidine derivatives.

U.S. Pat. No. 4,900,827 describes a process for preparing 4,6-bis(difluoromethoxy)pyrimidine derivatives in which a 4,6-dihydroxypyrimidine dialkali-metal salt is reacted with chlorodifluoromethane dissolved in acetonitrile or acetone in the presence of 0.05 to 1.1 mol of water per mol of 4,6-dihydroxypyrimidine dialkali-metal salt. A disadvantage of this process is that the reaction is carried out in a heterogeneous, three-phase system. That is to say, acetonitrile or acetone is the liquid phase, the 4,6-dihydroxypyrimidine dialkali-metal salt is a solid and the chlorodifluoromethane is partly dissolved and partly in the gas phase.

European Published Patent Application No. A 0468069 describes a process for preparing 4,6-bis(difluoromethoxy)pyrimidine derivatives proceeding from the corresponding 4,6-dihydroxypyrimidine by reaction with chlorodifluoromethane at normal pressure in the presence of sodium hydroxide dissolved in dioxane. A disadvantage of this process is that an appreciable amount of chlorodifluoromethane is used and, consequently, the process is not ecological. In addition, dioxane is not suitable as a solvent in the production.

BROAD DESCRIPTION OF THE INVENTION

An object of the invention is to provide a more ecological process for producing 4,6-bis(difluoromethoxy)pyrimidine derivatives which can be carried out under milder reaction conditions, such as, lower temperature. Other objects and advantages of the invention are set out herein or are obvious herefrom to one skilled in the art.

The objects and advantages of the invention are achieved by the process of the invention.

According to the invention, the process is carried out in such a way that a 4,6-dihydroxypyrimidine dialkali-metal salt of the general formula:

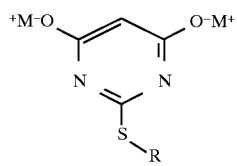

is reacted under pressure with chlorodifluoromethane in a solvent selected from the group consisting of the ketones, in the presence of a base and a phase-transfer catalyst and in the presence of 40 to 100 mol of water per mol of the 4,6-dihydroxypyrimidine dialkali-metal salt of the general formula II, to form the final product of the formula:

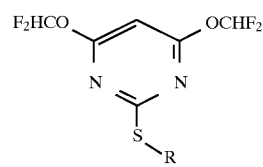

The substituent R is either $C_{1-4}$-alkyl or optionally substituted phenyl or benzyl. $C_{1-4}$-alkyl can be methyl, ethyl, propyl, isopropyl, butyl, isobutyl or tert-butyl. Suitable as substituents for phenyl or benzyl are, for example, $C_{1-4}$-alkyl, halogens, such as F, Cl, Br or I, nitro and $C_{1-4}$-alkoxy, such as methoxy, ethoxy, propoxy or butoxy. Preferably, R is methyl.

The educts, the 4,6-dihydroxypyrimidine dialkali-metal salts, are commercially obtainable or can be synthesized according to European Published Patent Application No. A0529631.

Suitable solvents selected from the group consisting of the ketones are, for example, acetone, methyl ethyl ketone, diethyl ketone, methyl isopropyl ketone or methyl isobutyl ketone. Preferably, acetone is used as the solvent.

An alkali-metal or alkaline-earth-metal hydroxide can be used as the base. Lithium hydroxide, sodium hydroxide or potassium hydroxide can be used as the alkali-metal-hydroxide. Calcium hydroxide or magnesium hydroxide can be used as the alkaline-earth-metal hydroxide. Preferably, sodium hydroxide is used as the base.

Expediently, the base is used in an amount of 2 to 8 mol, preferably of 4.6 to 6 mol, per mol of 4,6-dihydroxypyrimidine dialkali-metal salt.

Quaternary ammonium salts are generally suitable as the phase-transfer catalysts. The preferred phase-transfer catalysts are benzyltrimethylammonium chloride, tetrabutylammonium chloride, tetramethylammonium bromide and tetramethylammonium chloride. In particular, tetramethylammonium chloride is preferably used as the phase-transfer catalyst.

The phase-transfer catalysts can be used in an amount of 0.05 to 0.2 mol, preferably of 0.1 to 0.15 mol, per mol of 4,6-dihydroxypyrimidine dialkali-metal salt.

The chlorodifluoromethane can be used in an amount of 2 to 6 mol, preferably of 3 to 4 mol, per mol of 4,6-dihydroxypyrimidine dialkali-metal salt.

The reaction is carried out in the presence of 40 to 100 mol of water, preferably of 60 to 90 mol, per mol of 4,6-dihydroxypyrimidine dialkali-metal salt.

The reaction is carried out under increased pressure, preferably at a pressure of 1 to 6 bar, in particular preference at a pressure of 2 to 5 bar. Expediently, the reaction is carried out at a temperature of 40° to 60° C., preferably of 45° to 55° C.

The 4,6-bis(difluoromethoxy)pyrimidine derivatives can be prepared in good yield with a small amount of chlorodifluoromethane by the process according to the invention. A further advantage is the mild reaction conditions, such as, low temperature and the short reaction time.

EXAMPLE

Preparation of 4,6-bis(difluoromethoxy)-2-methylthiopyrimidine

Moist sodium methylthiobarbiturate (242 g; 58.3 percent content; 0.698 mol), water (381 g; 21 mol), tetramethylammonium chloride (9.7 g; 0.0878 mol) and acetone (261 g) were introduced into an autoclave at 20° C. The autoclave was closed and filled with nitrogen. The mixture was heated to 46° C. while stirring vigorously and chlorodifluoromethane (115.3 g; 1.333 mol) was then fed in at a pressure of 3.1 bar. In the course of 1.5 hours, 25 percent-strength NaOH (246.6 g; 1.541 mol) was added at constant temperature. Acetone (261 g), chlorodifluoromethane (76.8 g; 0.889 mol) and 25 percent-strength NaOH (349 g; 2.181 mol) were then again added at 46° C. in the course of 2 hours. At the end of the reaction, the pressure was 4.3 bar. The reaction mixture was stirred for a further 1 hour and then cooled to 20° C. After letting down (absorption of the chlorodifluoromethane in acetone), the organic phase was separated, acetone distilled off and the residue extracted with chlorobenzene (275 g) and water (100 g). In total, 106.3 g of 4,6-bis(difluoromethoxy)-2-methylthiopyrimidine, equivalent to a yield of 59 percent, was obtained.

What is claimed is:

1. A process for preparing a 4,6-bis(difluoromethoxy) pyrimidine derivative of formula:

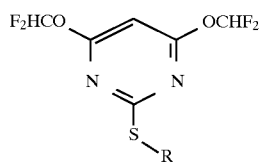

I wherein R is $C_{1-4}$-alkyl, optionally substituted phenyl or optionally substituted benzyl, comprising reacting a 4,6-dihydroxypyrimidine dialkali-metal salt of formula:

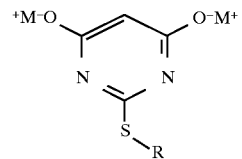

II wherein R has the above-stated meaning and M is an alkali-metal atom, under pressure with chlorodifluoromethane in a solvent selected from the group consisting of the ketones, in the presence of a base and a phase-transfer catalyst and in the presence of 40 to 100 mol of water per mol of the 4,6-dihydroxypyrimidine dialkali-metal salt of formula II to form the final product of formula I.

2. The process according to claim 1, wherein acetone is used as the solvent selected from the group consisting of the ketones.

3. The process according to claim 2, wherein an alkali-metal hydroxide is used as the base.

4. The process according to claim 3, wherein 2 to 6 mol of chlorodifluoromethane are used per mol of 4,6-dihydroxypyrimidine dialkali-metal salt.

5. The process according to claim 4, wherein the reaction is carried out at a temperature of 40° to 60° C.

6. The process according to claim 5, wherein the reaction is carried out at a pressure of 1 to 6 bar.

7. The process according to claim 6, wherein tetramethylammonium chloride is used as the phase-transfer catalyst.

8. The process according to claim 1, wherein an alkali-metal hydroxide is used as the base.

9. The process according to claim 1, wherein 2 to 6 mol of chlorodifluoromethane are used per mol of 4,6-dihydroxypyrimidine dialkali-metal salt.

10. The process according to claim 1, wherein the reaction is carried out at a temperature of 40° to 60° C.

11. The process according to claim 1, wherein the reaction is carried out at a pressure of 1 to 6 bar.

12. The process according to claim 1, wherein tetramethylammonium chloride is used as the phase-transfer catalyst.

13. The process according to claim 1 wherein the base is an alkali metal hydroxide or an alkaline earth metal hydroxide.

14. The process according to claim 13 wherein the reaction is carried out in the presence of 60 to 90 mol of water per mol of 4,6-dihydroxypyrimidine dialkali-metal salt.

15. The process according to claim 14 wherein the phase transfer catalyst is a quaternary ammonium salt.

* * * * *